(12) United States Patent
Patel

(10) Patent No.: US 11,931,379 B2
(45) Date of Patent: Mar. 19, 2024

(54) STABLE FOAMING COMPOSITION AND METHOD OF USE

(71) Applicant: Johnson & Johnson Consumer Inc., Skillman, NJ (US)

(72) Inventor: Jiger Patel, Somerset, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 15/370,285

(22) Filed: Dec. 6, 2016

(65) Prior Publication Data

US 2017/0173075 A1   Jun. 22, 2017

Related U.S. Application Data

(60) Provisional application No. 62/270,889, filed on Dec. 22, 2015.

(51) Int. Cl.
| | |
|---|---|
| *A61K 33/30* | (2006.01) |
| *A61K 8/04* | (2006.01) |
| *A61K 8/31* | (2006.01) |
| *A61K 8/37* | (2006.01) |
| *A61K 8/891* | (2006.01) |
| *A61K 8/92* | (2006.01) |
| *A61K 9/00* | (2006.01) |
| *A61K 31/192* | (2006.01) |
| *A61K 31/58* | (2006.01) |
| *A61K 31/695* | (2006.01) |
| *A61M 35/00* | (2006.01) |
| *A61Q 19/00* | (2006.01) |

(52) U.S. Cl.
CPC .............. *A61K 33/30* (2013.01); *A61K 8/046* (2013.01); *A61K 8/31* (2013.01); *A61K 8/37* (2013.01); *A61K 8/891* (2013.01); *A61K 8/922* (2013.01); *A61K 8/927* (2013.01); *A61K 9/0014* (2013.01); *A61K 31/192* (2013.01); *A61K 31/58* (2013.01); *A61K 31/695* (2013.01); *A61M 35/003* (2013.01); *A61Q 19/005* (2013.01); *A61K 2800/87* (2013.01)

(58) Field of Classification Search
CPC .......... A61K 33/30; A61K 8/046; A61K 8/31; A61K 8/37; A61K 8/891; A61K 8/922; A61K 8/927; A61K 9/0014; A61K 31/192; A61K 31/58; A61K 31/695; A61K 2800/87; A61M 35/003; A61Q 19/005
See application file for complete search history.

(56) References Cited

U.S. PATENT DOCUMENTS

| | | | |
|---|---|---|---|
| 4,781,914 A | 11/1988 | Deckner | |
| 5,762,945 A | 6/1998 | Ashley | |
| 6,627,178 B1 | 9/2003 | Cawthon | |
| 6,803,045 B1 | 10/2004 | Goldberg | |
| 6,946,139 B2 | 9/2005 | Henning | |
| 7,108,860 B2* | 9/2006 | Dueva ...................... | A61K 8/73 424/400 |
| 8,609,784 B2* | 12/2013 | Hessefort ................. | A61K 8/88 252/405 |
| 8,618,081 B2* | 12/2013 | Tamarkin ............. | A61K 9/0014 424/400 |
| 8,821,841 B2 | 9/2014 | Nguyen Kim et al. | |
| 8,945,516 B2* | 2/2015 | Tamarkin ............. | A61K 9/0014 424/114 |
| 8,999,391 B2* | 4/2015 | Adamo .................. | A61K 8/731 424/488 |
| 9,144,535 B1 | 9/2015 | Daly et al. | |
| 9,144,536 B1 | 9/2015 | Daly et al. | |
| 2007/0134174 A1* | 6/2007 | Irwin ...................... | A61K 8/03 424/59 |
| 2007/0269389 A1* | 11/2007 | Fuscelli Pytel ...... | A61K 8/0229 424/59 |
| 2009/0041680 A1 | 2/2009 | Tamarkin et al. | |
| 2010/0129303 A1* | 5/2010 | Dueva-Koganov ...... | A61K 8/29 424/60 |
| 2010/0260700 A1* | 10/2010 | Dop ...................... | A61K 8/891 424/78.03 |
| 2012/0093748 A1* | 4/2012 | Fares ..................... | A61K 8/365 424/62 |
| 2012/0225106 A1 | 9/2012 | Ross et al. | |

FOREIGN PATENT DOCUMENTS

| | | |
|---|---|---|
| DE | 102008048188 A | 4/2010 |
| DE | 102010063060 A | 6/2012 |
| EP | 1604632 | 12/2005 |
| WO | WO 2015/113307 A | 8/2015 |

OTHER PUBLICATIONS

European search report and opinion dated Feb. 27, 2017, for EP 16206483.6.
Mintel; "Fluid Foundation Corrector SPF 15"; Laboratoires Dermatologiques Ducray; http://www.gnpd.com; Jun. 2015; 7 pages.

* cited by examiner

*Primary Examiner* — Robert A Wax
*Assistant Examiner* — Olga V. Tcherkasskaya
(74) *Attorney, Agent, or Firm* — Samuel J. Gee

(57) ABSTRACT

Compositions, systems and methods of dispensing compositions for treating skin conditions, the compositions including an inorganic compound and having desirable viscosity, spreadability and foam drainage profiles.

9 Claims, 2 Drawing Sheets

… … …

STABLE FOAMING COMPOSITION AND METHOD OF USE

CROSS-REFERENCE TO RELATED APPLICATIONS

The present application claims the benefit of U.S. Patent Application No. 62/270,889, filed on Dec. 22, 2015, the complete disclosure of which is hereby incorporated by reference for all purposes.

FIELD

The present invention relates to skin care compositions, particularly topical skin care compositions for treatment of skin, including treatment of diaper rash on infants and toddlers. The invention includes compositions, methods of application, and applicators for dispensing such compositions.

BACKGROUND

Diaper rash is a common problem affecting babies and toddlers. It is generally associated with increased bacteria on and in the diapering region of babies. Currently, the most popular and commonly used method for treating diaper rash is to apply a thick cream including active components and include a moisture barrier on the skin. These compositions are typically spread by hand to ensure coverage on the desired area in the appropriate thickness and providing enough coverage to treat the affected area. Other methods include using an applicator to contact the affected skin, by releasing some of the composition and rubbing the skin with the applicator. These methods require contact of the affected skin with a device or with a user's skin or hand, which not only presents a risk for contamination but also may cause further pain or discomfort to the affected skin.

While effective, these methods require the user's hand or fingers to contact not only the diaper rash cream itself but also the affected area of the baby's skin to spread the composition properly. In addition, such treatments tend to be very thick, and are thereby difficult to accurately and adequately spread to the affected area of skin. There exists a need to provide a composition that is effective, spreadable, and easy to apply while maintaining pleasing aesthetic.

A stable viscous foaming composition has now been discovered that contains oil soluble inorganic compound, such as zinc oxide, and high levels of organic oils. The composition also optionally contains a foaming agent, a propellant, an emulsifier and a polymeric thickener.

SUMMARY

In one embodiment, there is a composition including an ester; an oil; and a flake resin. The composition may further include components such as an inorganic compound. The invention may further include a system including a composition, which includes an ester; an oil; a flake resin; a propellant; and a dispenser having an exit port that is biased in a closed position and is openable via an opening action; where the composition is contained within the dispenser.

Other aspects of the invention relate to a method of dispensing a composition from a dispenser including the steps of: aligning an exit port of the dispenser at a target site, where the exit port is biased in a closed position and is openable upon activation, the dispenser including therein a propellant and a composition including: an ester; an oil; and a flake resin; and activating the exit port at the target site to open the exit port, thereby dispensing a desired amount of the composition at the target site.

DETAILED DESCRIPTION

Figure 1:
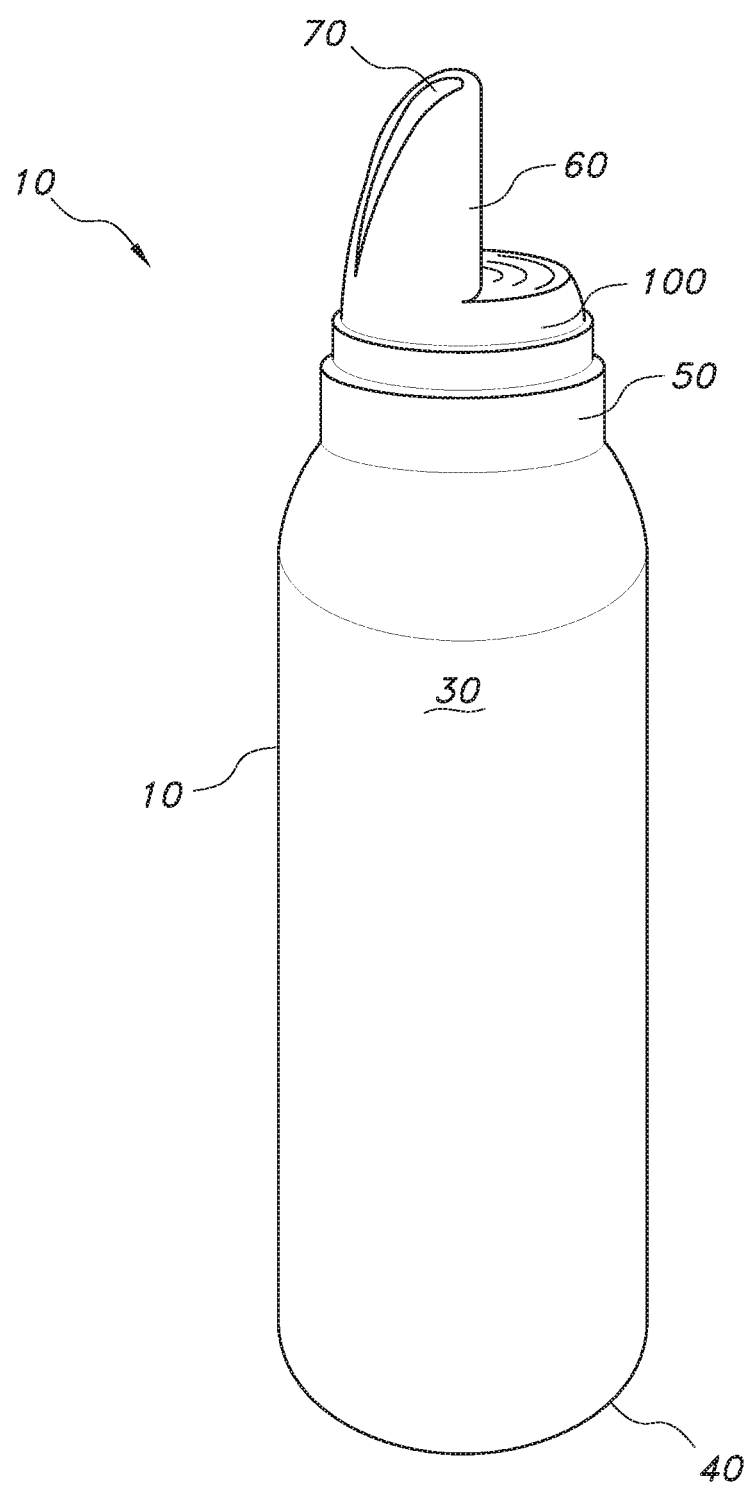
FIG. 1 is a side view of an exemplary dispenser useful in the present invention.

The present invention relates to and includes compositions, methods and devices for treating skin conditions, including, for example, diaper rash in infants and toddlers, as well as adult individuals, such as incontinent individuals. However, the products described herein may be useful for treating any number of skin conditions that may be treated by application of the composition described herein. The compositions provided herein not only include components useful to actively treat and protect the skin surface, but also include components useful to provide the desired viscosity and spreadability. In addition, the invention includes a system and an apparatus for application of the desired composition. Further, the invention includes method of treatment of diaper rash or other skin conditions.

As used herein, the term "diaper rash" includes and refers to contact dermatitis in the diapering region of a human individual, such as the region that may be exposed to prolonged contact with feces or urine. Diaper rash generally references an inflammatory reaction localized to the area of skin usually covered by the diaper, which may have many causes, including infections (yeast, bacterial, or viral), friction irritation, chemical allergies (perfumes, soaps), sweat, decomposed urine, and plugged sweat glands. Although referenced herein as "diaper rash", the skin region to be treated includes regions that may not be adjacent to or covered by a diaper, and may include skin regions that experience rash or other infections to be treated through application of a composition described herein. The area of the skin experiencing such infection or inflammatory reactions (including diaper rash) is referred to as the affected area, and may include evidence of infection or inflammation, or may have no visible symptoms. The affected area is any skin area where treatment is required, including the diapering regions of individuals.

As used herein, "topically applying" means directly laying on or spreading on outer skin, e.g., by use of the hands or an applicator such as a wipe, roller, or spray.

Compositions described herein are desired to be spread over the affected area of skin, and should have one or more desired characteristics described below, including a desired viscosity level, desired spreadability, and a desired foaming level and duration. It is known to use a spray applicator to apply zinc oxide-containing sunscreen, but in these products, the composition has a high water content of greater than 70% water, giving it a relatively low viscosity (e.g., about 500 cps to about 1,000 cps at room temperature) to allow it to be sprayed properly. Further, these sprayable sunscreens include a lower level of zinc oxide (from about 3-10%, generally about 6% by weight). The effect of these products is not to deliver a therapeutic effect, but rather to apply a sun-blocking product to the skin surface. The compositions herein are effective at applying a high level of a skin treatment agent to the skin and allowing it to be applied effectively and thoroughly. In some aspects, the viscosity of the present compositions may be from about 5,000 cps to about 50,000 cps at room temperature (e.g., approximately 24-25 degrees C.), and in other aspects the viscosity may be from about 10,000 cps to about 40,000 cps at room temperature, or from about 10,000 cps to about 25,000 cps at room temperature. This viscosity level is measured prior to being dispensed from a dispensing apparatus, such as a dispenser that foams the composition upon dispensing.

Useful compositions of the present invention may include one or more of the following: active components, skin protectants, moisture barriers, spreading agents, viscosity modifiers, preservatives, emulsion stabilizers, humectants, emollients, emulsifiers and in some embodiments, includes a propellant for dispensing a treatment composition from a dispenser such as an aerosol dispenser. The compositions described herein, when used to treat a rash or other similar skin condition, may include a relatively high level of an inorganic component, as will be described below, where the inorganic component is suspended in the composition. For example, it may be desired that there be about 10% to about 15% by weight of an inorganic component dispersed throughout the composition.

The composition is also desirably flowable enough to be dispensed from a dispenser, while also viscous enough to be spread on the affected skin without running off of the skin after application. Desirable viscosity ranges are described below, but in general the product should be capable of being dispensed through a dispenser, spread onto a region of the skin, and remain on the skin for a desired length of time. It is desirable that the composition be or include a water-in-oil emulsion.

Finally, the composition should be foamable to allow for spreading and application onto the skin, as such, it may be desirable to include a foaming agent or foam stabilizer to allow for the product to foam and maintain foaming for a time desired to apply to the target region of the skin. In some embodiments, the product forms a foamed product which is stable for at least about 30 seconds and may maintain foaming for about two minutes after it is dispensed from a dispenser. These and other characteristics and properties will be described in greater detail below.

Skin Treatment Compositions

The composition includes an oil base, and is desirably a water-in-oil emulsion, which is intended to be applied directly to an affected area of skin, as described above. It is particularly desired that the composition not be an oil-in-water emulsion, but rather it be a water-in-oil emulsion. The use of oil in the composition is beneficial to sequester the inorganic compound (such as zinc oxide), allowing it to give a smooth and even distribution of the inorganic compound during application. The composition includes an oil phase, an aqueous component, at least one inorganic compound, and optionally includes a foaming agent and/or a propellant.

The composition exhibits a fluid-like behavior having a desired viscosity level, such that it is flowable and capable of being dispensed and applied directly onto the affected skin. In addition, the composition is a foam when dispensed from the dispenser, that is, it has a plurality of small bubbles formed within the composition, where the bubbles are desirable evenly dispersed throughout the composition. The foam desirably has properties described in greater detail below. The composition has a suitable viscosity to allow for flowing and spreading but should not have so low a viscosity so as to run off the affected skin area. In desired embodiments, the composition has a viscosity prior to dispensing from a dispenser of about 5,000 cps to about 50,000 cps at room temperature. More specifically, the composition has a viscosity of about 10,000 cps to about 25,000 cps at room temperature prior to dispensing from a dispenser.

The composition according to the invention preferably comprise up to 60% by weight of the oil phase, in which case they are water/oil emulsions. The oil phase according to the invention may be present in an amount of from about 10% to about 50% by weight of the composition. More desirably, oil phase is present in an amount of about 20% to about 50% by weight of the composition, and even more preferably from about 25% to about 40% by weight of the composition.

The oil phase includes one or more oil compounds, including emollients used for the prevention of or relief of skin dryness and for skin protection as well as solubilizing the inorganic compounds for diaper rash treatment described in greater details below.

As used herein, "oils" means organic, hydrophobic compounds that are liquid at ambient temperature and silicone-based materials. As used herein, "silicones" means chemically or physically cross-linked molecules comprising at least one siloxane repeat unit.

Examples of organic oils include various hydrocarbons (straight or branched chain alkanes or alkenes, ketone, diketone, primary or secondary alcohols, aldehydes, sterol esters, alkanoic acids, turpenes, monoesters), such as those having a carbon chain length ranging from C6-C38, such as C6-C18. Other organic oils include esters of fatty acids with alcohols of low carbon number, e.g. with isopropanol, propylene glycol or glycerol, or esters of fatty alcohols with alkanoic acids of low carbon number or with fatty acids, and polyol esters.

Specific non-limiting examples of oils include without limitation, natural oils (e.g. olive oil, sunflower oil, soybean oil, groundnut oil, rapeseed oil, almond oil, palm oil, coconut oil, palm kernel oil, castor oil and the like), castor oil, mineral oil, petrolatum, vegetable oils (e.g. triglycerides such as caprylic or capric triglyceride), esters of an alcohol (glycerol or other than glycerol including diesters or other branched esters) and a fatty acid or fatty alcohol, and various natural waxes including shea (*Butyrospermum parkii*) butter, lotus wax; beeswax, insect waxes, sperm whale oil, lanolin, vegetable waxes such as canauba wax, jojoba oil, candelilla wax; mineral waxes such as paraffin wax; and synthetic waxes such as cetyl palmitate, lauryl palmitate, cetostearyl stearate, and polyethylene wax.

Other oils include for example esters such as isopropyl palmitate, isopropyl myristate, isononyl isononanoate (such as WICKENOL 151 available from Alzo Inc. of Sayreville, NJ), C12-C15 alkyl benzoates (such as FINSOLV TN from Innospec Active Chemicals), pentaerythritol tetraoctanoate, dipropylene glycol dibenzoate, PPG-15 stearyl ether benzoate, 2-ethylhexyl isostearate, alkyl isononanoate such as isotridecyl isononanoate, octyldodecanol, isoeicosane, 2-ethylhexyl cocoate PPG-2-Myristyl Ether Propionate, hydrogenated metathesis products of unsaturated triglycerides, and combinations thereof and other hydrocarbons, such as paraffin oil, squalane and squalene, and diethylhexylcyclohexane. Further examples of oils include functional oils such as vitamin E acetate.

Yet other oils include for example silicone oils, such as dimethylpolysiloxanes (dimethicone), diethylpolysiloxanes, diphenylpolysiloxanes and mixed forms thereof.

It has traditionally been thought that certain oil-based components, such as mineral oil and lanolin are unsuitable in foaming compositions. That is, such oil-based components traditionally were thought to disrupt bubble formation and therefore impact the foaming properties of the composition (described in greater detail below). The present invention includes these components in a suitably foaming composition. In certain aspects, it is desired to include a combination of a readily emulsifiable oil component and a not readily emulsifiable oil component. One suitable readily emulsifiable oil component includes an ester, which offers a number of benefits. For example, esters are capable of solubilizing lipophilic cosmetic raw materials, such as sunscreen agents and volatile silicones, and they have high positive spreading coefficient, anti-tack agent and anti-whitening properties.

Examples of components that are not readily emulsifiable include mineral oil and petrolatum, which is beneficial in that it has a long wet feel duration and is able to serve as a weak wetting agent for water insoluble products. In combination, it has been found by the present inventors that esters may be useful to impart a dry lubricating feel even in the presence of large amounts of mineral oil or petrolatum, and is a wetting agent and auxiliary suspending agent for water insoluble products.

The inorganic compound includes compounds suitable for treating diaper rash or other skin inflammation/infection, or may include other agents such as sun filter agents, color cosmetic agents, and other inorganic compounds suitable for application to human skin. The inorganic compound is desirably present in an amount of from about 5% to about 25%, and more particularly about 10% to about 20%, and most desirably about 13% to about 15% by weight of the final composition. The inorganic compounds may be suspended in the final composition, and are desirably distributed in the composition in a substantially homogeneous manner after dispensed from a container. To achieve even dispersion within the composition, it is desired to include a suitable level of oil to sequester and to solubilize an inorganic compound and disperse it throughout the composition.

As described below, to dispense the composition in a suitable foamed manner, it may be desired to shake or otherwise agitate a container with the composition to disperse the components therein, including the inorganic compounds therein. The dispenser is preferably an aerosol dispenser, and therefore one or more propellants are desired in the composition. It is desired that the inorganic components be substantially homogeneously distributed in the composition as it is being dispensed from a dispenser.

The inorganic compound may include, for example, skin protectants such as zinc-based compounds, including, for example, zinc oxide, or may include cationic zinc compounds. Other inorganic compounds include titanium dioxide, iron oxides, silicone oxides, or other metal (e.g., transition metal, such as crystalline transition metal) oxides. Such inorganic compounds are typically solid particles having a diameter from about 0.1 micron to about 10 microns. The inorganic compound is desirably present in an amount from about 10% to about 20% by weight of the composition, and more desirably about 10% to about 15% by weight of the composition. Optional sun filter components may include, for example titanium containing compounds. Suitable components may include those described in U.S. Pat. Nos. 9,144,536 and 9,144,535, both of which are incorporated by reference herein in their entireties.

The compositions of the present invention are applied topically to human skin. Accordingly, the composition may further include cosmetically acceptable topical ingredients as known in the personal care art for use with the composition of the present invention of the water-in-oil emulsion type. Examples of suitable additional active agents include: skin lightening agents, darkening agents, additional anti-aging agents, tropoelastin promoters, collagen promoters, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, odor-control agents such as odor masking or pH-changing agents, and the like.

The cosmetically active agent may be present in a composition in any suitable amount, for example, when used, it may be present in an amount of from about 0.0001% to about 20% by weight of the composition, e.g., about 0.001% to about 10% such as about 0.01% to about 5%. In certain embodiments, in an amount of 0.1% to 5% and in other embodiments from 1% to 2%.

The composition may include a foam booster in an amount suitable to aid the composition in forming the desired level of foaming and ultimately spreading and adherence to the skin. The foam booster may include a resin, such as a siloxysilicate, including trimethylsiloxysilicate (commercially available as Dow Corning® MQ-1600 flake resin). Other silicates may be useful as foam boosters. The foam booster may be present in an amount of about 0.2% to about 1.0% by weight of the final composition. More desirably, the film former is present in an amount of about 0.5% by weight of the final composition. The use of a flake resin such as the aforementioned siloxysilicate has traditionally been used as a sun protection factor ("SPF") booster and waterproof barrier in sunscreens, but the present inventors have surprisingly discovered that the use of such a flake resin acts as a foaming agent and improves the ultimate formulation used herein. Until the present invention, such flake resin was not known to provide a composition with foaming properties.

In embodiments using a flake resin, it may be useful to include one or more esters to dissolve the flake resin. The weight ratio of flake resin to ester is about 1:2 to about 2:1. Suitable esters include, for example, esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group of esters of aromatic carboxylic acids and saturated and/or unsaturated, branched and/or unbranched alcohols having a chain length of from 3 to 30 carbon atoms. Preferably, suitable esters, but not limited to, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil, glycerides (specifically triglycerides) and alkyl benzoates. For example, C12-15 Alkyl Benzoate and Caprylic/Capric Triglycerides, may be individually useful.

The composition may also include an aqueous component, such as water or other similar aqueous component. Water may be present in an amount of from about 5% to about 65% by weight of the composition. More desirably, water is present in an amount of about 40% to about 60% by weight of the composition, and even more preferably from about 55-60% by weight of the composition.

The composition may include other components, including, for example, one or more skin conditioners, emollients, humectants, emulsifiers, thickeners, and emulsion stabilizers as desired. Suitable skin conditioners include, for example, hexanediol, caprylyl glycol, tropolone, oat kernel extracts, and cationic polymers, including polyquarterniums, cationic guar, and the like. Skin conditioners may be present in an amount of from about 0.1% to about 1.0% by weight of the composition. The amount and selection of conditioners should be sufficient to impart additional attributes, such as gloss and softness to the skin that are suitable for use in this invention.

Suitable emollients include, for example, isopropyl palmitate, shea butter, mineral oil, lanolin, dicaprylyl carbonate, alkyl benzoates, including C12-15 alkyl benzoate, petrolatum, hexyldecyl stearate and plant, nut, and vegetable oils such as macadamia nut oil, rice bran oil, grape seed oil, palm oil, prim rose oil, hydrogenates peanut oil, and avocado oil, pentylene glycol, caprylyl methicone, dicaprylyl carbonate, and octyldodecyl neopentanoate or mixture thereof. When used, emollients may be present in an amount of from about 5% to about 20% by weight of the composition. The amount and selection of emollient should be sufficient to dissolve the inorganic compounds while maintaining the stability of the composition. Additional emollients include compounds that help to maintain the soft, smooth, and pliable appearance of the skin (e.g., by remaining on the skin surface or in the stratum corneum to act as a lubricant).

Suitable humectants include, for example, glycerin, sorbitol or trehalose (e.g., α,α-trehalose, β,β-trehalose, α,β-trehalose) or a salt or ester thereof (e.g., trehalose 6-phosphate). When used, humectants may be present in an amount of from about 1% to about 5% by weight of the composition. The amount and selection of humectant should be sufficient increase the water content of the top layers of skin (e.g., hygroscopic compounds).

Suitable emulsifiers include, for example, polyglyceryl-2 dipolyhydroxystearate, polyglyceryl-3 diisostearate, glyceryl stearate, steareth-21, and polyacrylate-13/polyisobutene/polysorbate 20 or mixture thereof. When used, emulsifiers may be present in an amount of from about 1% to about 10% by weight of the composition.

Suitable thickeners include, for example, ammonium acrylolydimethyltaurate/vinylpyrrolidone copolymer, sodium acrylolydimethyltaurate/vinylpyrrolidone copolymer, and sodium polyacrylate. When used, thickeners may be present in an amount of from about 0.1 to about 10. The amount and selection of the thickener allows for stabilization of the composition while maintain the composition aesthetic and skin feel.

Suitable emulsion stabilizers include, for example, magnesium sulfate, and zinc stearate, among others. When used, emulsion stabilizers may be present in an amount of from about 1% to about 5% by weight of the composition.

The composition may be dispensed from an applicator, and it may include a propellant for aiding the dispensing from an applicator. When present, the propellant may be present in an amount suitable to aid in dispensing the product, and may vary in amount capable to dispense the composition. For example, the propellant may be present in an amount of about 4% to about 10%, or more desirably about 6% to about 7% by weight of the composition. When the composition is not dispensed from a dispenser requiring propellant, the propellant may be absent. Any desired propellants may be used, including those propellants described in U.S. Pat. No. 8,821,841, the contents of which are incorporated by reference herein in full. Propellants that may be particularly desired include, for example, propane, butane, isobutane, pentane, ethane, isopentane, pentane, methyl ether, difluoroethane, and combinations thereof. In one aspect, the propellant includes that available under the trade name Aeron-A-31 (commercially available from Dow Corning), which is a combination of propane, ethane, isopentane, and pentane. Where the viscosity of the composition is greater, the amount of the propellant required to adequately dispense the composition from the applicator may be higher (e.g., about 8% to about 10% by weight).

In one aspect, it was discovered that the composition including a combination of an oil, a flake resin and an ester provided suitable viscosity, foaming, and spreadability of the composition. Although the amounts of each may vary, in certain embodiments, it may be desired that the oil and ester be present in an amount of from about 50:50 (oil:ester) to about 25:75 (oil:ester) by weight.

Foaming Properties

The compositions described herein are desirably capable of forming a foamed composition when dispensed from the dispenser. While the compositions may be free of bubbles or substantially free of bubbles while in the dispenser and not being used, during dispensing of the composition, the composition is desirably a foamed composition. This may be aided by, for example, shaking or agitating the dispenser prior to dispensing the composition therefrom. When dispensed and applied to the affected skin, the composition should have a suitable foamed profile, which is to have a substantially even dispersion of small bubbles, the size being sufficiently small to create a dense foam structure. It is desired that the size of bubbles within the foamed composition does not vary more than about 100% with respect to other bubbles within the foamed composition. In other words, the relative sizes of the bubbles formed within the foamed composition may be substantially similar in size with each other. It is desired that the dispensed composition be at least substantially free of if not completely free of uneven sized bubbles, as described above. When the bubbles become too large and ultimately burst, this leaves an undesirably large void where no product is located. Visual inspection of the dispensed product may be useful in evaluating whether there is a proper foaming profile.

It is desired that the foamed composition include the plurality of bubbles therein and that the foam have a slow foam drainage time. That is, a majority of the bubbles in the foam should remain intact for at least about 30 seconds, or at least about 1 minute, or at least about 90 seconds, or at least about 2 minutes, or up to about 2 minutes. It is further desired that the foam have a substantially even deflation across the entire dispensed composition, such that the composition has a foam drainage of approximately the same rate throughout the dispensed area.

As described above, it has been surprisingly found that the compositions described herein can include a water-in-oil composition including a relatively high oil content (and low water content), and include components such as mineral oil and/or lanolin, while still maintaining proper and sufficient bubble formation. The inventors have discovered that the use of a flake resin is useful in maintaining bubble formation in the dispensed composition, allowing it to maintain the proper foaming profile described above. Flake resin may be used in combination with an ester component to dissolve the flake resin in the composition, and the composition may use an ester, an oil, and a flake resin in combination with each other to achieve a desirable profile.

Viscosity of Composition

The composition should have a desired viscosity to allow for proper dispensing from a container, while also maintaining viscosity after dispensing and applying to the skin. It is desired that the viscosity be high enough to maintain the product on the skin and avoid run-off, but not so high so as to restrict dispensing from a container as described below. Suitable viscosities of the composition may be from about 10,000 cps to about 40,000 cps (at room temperature) prior to dispensing from the dispenser. Although higher or lower viscosities may be appropriate in certain instances, for the treatment of diaper rash as described herein, the viscosity range of 10,000-40,000 cps at room temperature is preferred.

Method of Use

The inventive compositions described herein may be used by applying the composition directly to the skin of the infected individual, and specifically to the affected site on the skin of the individual. The composition is desirably substantially homogeneous at the time of application, therefore it may be useful to stir, agitate, shake, or otherwise mix the composition prior to application to the skin of the user. This may be achieved, for example, by shaking or agitating the dispenser (described below) sufficiently to achieve mixing of the components therein. In embodiments where a dispenser such as that described below is not used, the product may be shaken or stirred to a desired level of mixing prior to application. In some embodiments, the composition may be housed in a tube, and mixing may be achieved by squeezing or massaging a tube sufficiently prior to dispensing the product. In still other embodiments, the composition is substantially homogenous within the dispenser, and no mixing or agitation on the part of the user is required.

Once the user is satisfied that the product is substantially homogeneous or mixed to a sufficient degree of mixing, the user may then apply the product directly to the affected skin of the individual.

It is preferable to use an aerosol dispenser including the composition therein to deliver the composition. Aerosol foam dispensers are apparatuses which are suitable for the foaming of compositions (mechanic, hydraulic etc.), including those for industrial applications. Preferred foam dispensers are spray containers. It has been found that the compositions are particularly suitable for spraying from mechanical foam dispensers. In order to achieve good foam formation, the oil phases and aqueous phases are preferably mixed together mechanically, preferably by simple shaking, prior to foaming. As noted above, the composition may not be foamed while it is contained within the dispenser, but after shaking or agitating the dispenser and dispensing the composition therefrom, the composition is foamed. Typical aerosol dispensers are useful in the present invention and are known to those of ordinary skill in the art. One such suitable aerosol dispenser is described in U.S. Pat. No. 6,946,139, the contents of which are incorporated herein by reference in their entirety. The invention described herein includes a system, which includes a composition as described above and the dispenser described herein.

Figure 2:
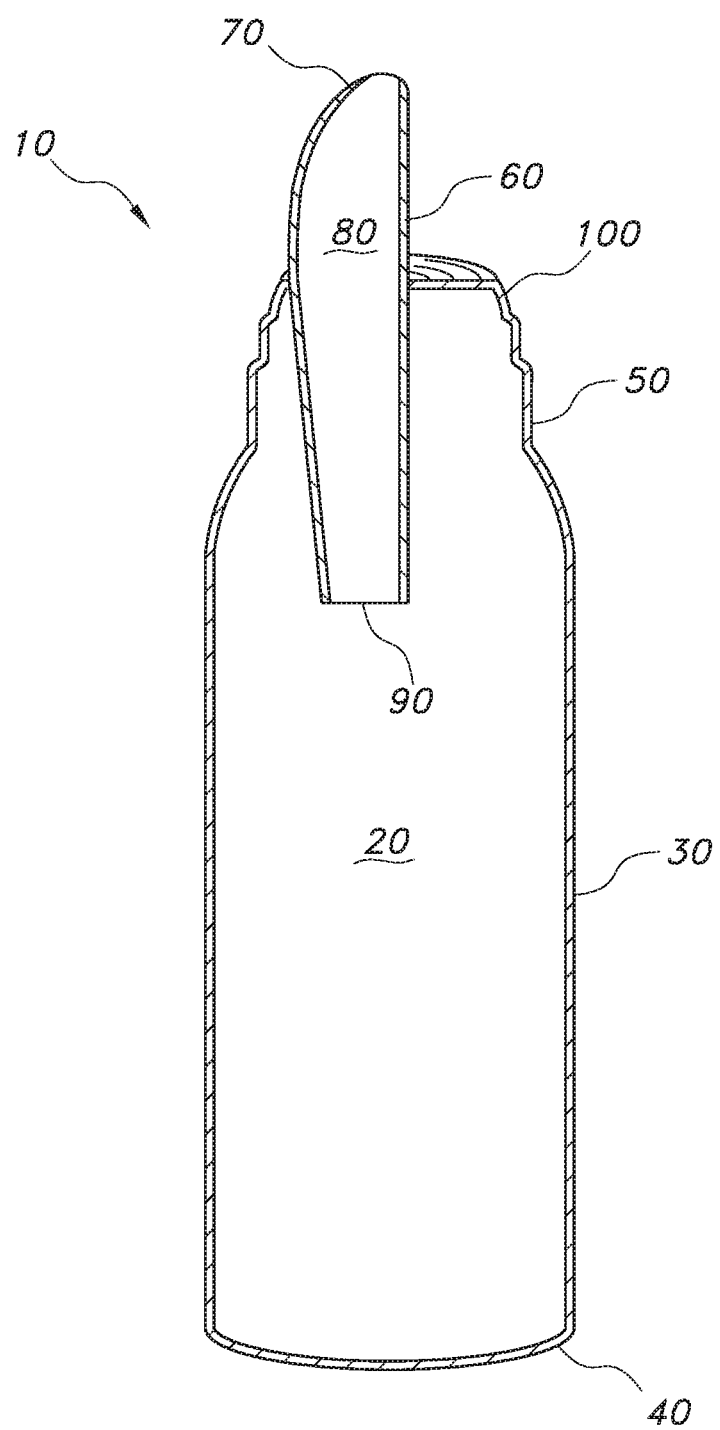
FIG. 2 is a cross-sectional view of the dispenser of FIG. 1.

Any dispensing container for holding the formulation described herein and dispensing the formulation may be used in the present invention. Without limitation, one useful dispenser includes an aerosol dispenser seen in FIG. 1. FIG. 1 shows the dispenser 10, and FIG. 2 shows a cross-section of the same dispenser 10. As can be seen in the Figures, the dispenser 10 is defined by an outer side wall 30, which may be any shape, including a cylindrical configuration as seen in the Figures. Outer side wall 30 may be rounded, square, bulbous, or any other desired shape or configuration. Side wall 30 may be made from any desired material, and is preferably a material that has a high degree of strength, such as metals or polymeric materials, including steel, aluminum, or other materials suitable for holding and dispensing materials under pressure. The side wall 30 may have any thickness, desirably having a thickness that increases its strength to a desired level such that it will not expand or contract during use. During use, the user may shake the container to mix the components therein, and may create a foaming within the container. Therefore, the outer side wall 30 should be strong enough to refrain from noticeable or undesirable levels of expansion or contraction.

The dispenser 10 is defined on its ends by a bottom surface 40 and upper surface 50, which are joined to the outer side wall 30 in a fluid tight configuration. The side wall 30, bottom surface 40 and upper surface 50 collectively define an open interior 20, into which the formulation to be dispensed is housed. The open interior 20 may be any shape or size desired, and in some embodiments it may take the shape of the outer side wall 30, upper surface 50 and bottom surface 40.

The upper surface 50 may include a dispensing head 60, which may form a part of the upper surface 50. The dispensing head 60 includes a dispensing opening 70, which is in fluid communication with a lumen 80, the lumen terminating in a distal opening 90. The distal opening 90 may be located within the open interior 20, to allow fluid components within the open interior 20 to enter the lumen 80 during use.

The dispensing head 60 also includes a valve 100, which may have any configuration to allow a user to manipulate the dispensing head 60. The lumen 80 may be biased in a closed configuration, such that fluid cannot pass through the lumen 80 without force acted thereon through an opening action, such as by opening the valve 100. In one embodiment, the valve 100 includes a finger receiving portion to allow a user to push a finger thereon, moving the lumen 80 such that it creates an open passageway from the distal opening 90 to the dispensing opening 70. Any desired valve 100 configuration may be used, including those described in U.S. Pat. No. 6,627,178, the entire contents of which are incorporated by reference herein. The finger receiving portion may be located adjacent to the dispensing opening 70.

For dispensers of the type described in FIGS. 1-2, the user will invert the dispenser 10, such that the dispensing opening 70 is facing downward, and may be at or near the target site, such as the diapering region of a baby. Other configurations, including those described in the aforementioned U.S. Pat. No. 6,627,178 may be used, including spray dispensers, or dispenser that include a hose or other conduit disposed within the open interior 20 of the dispenser.

In use, the user will pick up the dispenser, and may agitate or shake the dispenser to fully mix the components therein for use. Once the composition has been shaken or agitated sufficiently (e.g., from about 1 second to about 5 seconds or to about 10 seconds of agitation), it may be dispensed onto the affected area of skin. The user aims the dispensing opening 70 of the dispenser 10 at or near the affected area of skin, desirably without making contact with the skin and the dispenser. Therefore, in one method of use, the composition is dispensed without contacting the target skin with any component of the dispenser 10. In previous attempts, for example, in U.S. Pat. No. 6,803,045, an applicator is used to dispense product by contacting the applicator with the target skin. Desirably, in the present embodiment, there is no contact of the target skin with the dispenser 10 or any components of the dispenser 10.

Once the dispenser 10 is aligned or aimed at the target site, the user opens the valve by an opening action or activation action (e.g., by pressing a finger trigger) so as to open the valve, which allows the composition therein to be forced under pressure through the lumen and out the dispensing opening 70 of the port. The composition will be dispensed at a desired velocity, governed and guided by the amount and type of propellant within the dispenser. The composition is applied to the affected skin in the amount desired by the user and with the coverage desired over the skin. In desired embodiments, the composition is applied to fully cover the target region or affected area of the skin.

The user may apply one layer of the composition to the affected area of skin or may apply more than one layer. Further, the user may apply the composition to only the affected area of skin or may apply to the affected area and surrounding healthy (unaffected) areas of skin. Once applied, the composition may be allowed to sit and spread through the force of gravity, or a user may spread the composition with the hand or finger, or with a spreading tool. As the product sits on the surface of the skin, the foamed product will begin to experience foam drainage, described below, where the bubbles within the foamed composition begin to burst, and the composition becomes substantially collapsed, and therefore substantially free of visible bubbles. Proper foam drainage is understood by those of skill in the art, and although complete freedom from bubbles is desired, it is understood that the term "substantially free of visible bubbles" allows for a minimal amount of visible bubbles in the collapsed product. It is desired that at least about 99% of the bubbles formed upon initial dispensing of the product be burst, with about 1% or less of the initial bubbles remaining. The process of foam drainage may be from about 30 seconds to about 90 seconds or about 2 minutes. The foam structure, as is discharged from the pressurized container, is ruptured as the propellant is released from the foam body. The gas propellants create high volume of vigorous and relatively long lasting bubbling in the composition as discharged. Such compositions are unique in that the foam formed by the compositions is flowable and easily spreadable when applied and rubbed onto the skin and impart a pleasant cooling sensation.

Once a sufficient amount of composition is applied to the surface of the skin, the user may apply clothing or a diaper to the region of the skin, or allow the composition to sit undisrupted for a desired length of time. It is desired that the composition fully cover the affected region of skin, so as to allow the inorganic compound in the composition to contact the affected region of skin. In the case of diaper rash, the inorganic compound may be a zinc-containing compound, such as zinc oxide, which may treat the skin and protect the skin from further irritation and discomfort. In other embodiments, the composition may include other treatment agents, such as moisturizers, sunscreens, cleansers, and the like, which perform their own desired task on the surface of the skin.

The container may include sufficient composition to allow for multiple uses, and may include sufficient composition to be dispensed at least 5 times, or at least 15 times, or at least 25 times to sufficiently treat an affected region of skin each use. When the user releases the trigger, the valve in the dispenser is closed, and therefore the composition remains within the dispenser until the user opens the valve again. It is desired that the interior of the dispenser be sufficiently air-tight so as to allow the product to have a desired shelf life. The composition is advantageously stable over a typical commercial shelf life despite the higher amount of oils and low amount of emulsifiers. Little, preferably no, phase separation occurs in the composition over four weeks, eight weeks, six months, twelve months, eighteen months or twenty-four months.

The present invention further comprises a method of improving the barrier function and moisturization of skin by applying to skin in need of improving skin barrier function and moisturization the composition of the invention. The method comprises for example topically applying the composition to skin in need of improving skin barrier function and moisturization. Such topical application may be to any skin in need of treatment on the body.

In some embodiments, the invention may include the base formulation, without an active or other component such as the inorganic compound. That is, the base formulation may include, for example, a combination of the flake resin, ester and oil, as described above and in the amounts and/or ratios described above. The base formulation may provide a foamable chassis for a composition, such as a cleanser, a moisturizer or lotion, a sunscreen, or other uses including the foamable chassis. The foamable chassis described herein may include other components, for example, a cleansing component, or a moisturizing component, or a sunscreen component.

EXAMPLES

A number of different samples were prepared and tested for, among other properties, consistency, foaming, applicability, spreadability, effectiveness, and viscosity. As will be described below, the inventors have discovered that certain components were ineffective to prepare a suitable foaming composition, and it was surprisingly discovered that the use of a flake resin in combination with certain oils allowed for suitable foaming, viscosity, and spreadability.

Inspections were made by visual inspection, looking for evenly spread small bubbles in the dispensed product, where the bubbles were maintained in the composition for at least about 30 seconds after dispensing. Viscosity was measured for the composition prior to dispensing from the dispenser at room temperature.

Each Example discussed herein was prepared by conventional emulsion mixing process. For instance, the water and oil phase was first prepared first then subsequently mixed to create emulsions containing various combinations of ingredients listed in the below Tables.

Formulations A-V below were prepared, and the viscosity of each Formulation was measured using the Brookfield RVDV-II+Pro viscometer at ambient temperature following the procedure described below. Once prepared, the formulation was placed in a 4 oz graduated jar, which was then put into the following temperature/stability chambers (VWR Scientific Products Model 1545 at 40° C. and 50° C. respectively, GE model number GDSCOKCXMRWW at 4° C.) and a lab bench top as an ambient temperature (approximately 25° C.). After the stability time window was reached (e.g. 4 weeks), the viscosity was measured, results as described below. Visual inspection of the formulation both prior to dispensing from an aerosol container and after dispensing was conducted.

TABLE 1

Examples A-E

| INCI | A % | B % | C % | D % | E % |
|---|---|---|---|---|---|
| Water | 50.75 | 51.10 | 44.60 | 49.80 | 52.60 |
| Cetyl Hydroxyethylcellulose | 0.15 | 0.30 | 0.30 | 0.30 | 0.30 |
| Glycerin | 5.00 | 5.00 | 5.00 | 5.00 | 5.00 |
| Magnesium Sulfate, Anhydrous | 1.00 | 1.00 | 1.00 | 1.00 | 1.00 |
| 1,2-Hexanediol; Caprylyl Glycol; Tropolone | 0.50 | 0.50 | 0.50 | 0.50 | 0.50 |
| Zinc Stearate | 0.80 | 0.80 | 0.80 | 0.80 | 0.50 |
| C9-15 Alkyl Phosphate | 3.00 | 3.00 | 3.00 | 3.00 | 0.00 |
| *Butyrospermum Parkii* (Shea) Butter | 3.00 | 3.00 | 3.00 | 3.00 | 2.00 |
| Polyglyceryl-2 Dipolyhydroxystearate | 1.05 | 1.05 | 1.05 | 2.00 | 3.00 |
| Polyglyceryl-3 Diisostearate | 0.65 | 0.65 | 0.65 | 1.00 | 2.00 |
| Beeswax | 1.50 | 0.00 | 1.50 | 0.00 | 0.00 |
| Isopropyl Palmitate | 9.00 | 5.00 | 12.00 | 5.00 | 5.00 |
| Dicaprylyl Carbonate | 9.00 | 5.00 | 0.00 | 5.00 | 5.00 |
| Microcrystalline Wax | 1.50 | 1.50 | 1.50 | 1.50 | 1.00 |
| Zinc Oxide | 13.00 | 13.00 | 13.00 | 13.00 | 13.00 |
| *Avena Sativa* (Oat) Kernel Extract; Glycerin; Water | 0.10 | 0.10 | 0.10 | 0.10 | 0.10 |
| Citric Acid | 0.00 | 0.00 | 0.00 | 0.00 | 0.00 |
| Lanolin |  | 4.00 | 0.00 | 4.00 | 4.00 |
| C12-15 Alkyl Benzoate |  | 5.00 | 12.00 | 5.00 | 5.00 |

Examples A-E were prepared in the method described above with the components set forth in Table 1. Example A was found to be unstable at Freezing Temperature conditions (FT), e.g. −5° C. to 0° C., further, the formulation was unstable due to phase separation, and its viscosity was not measureable. Example B had a viscosity greater than 40,000 cps, which was deemed to be too high. Example C was unstable. Example D was too viscous, having a viscosity that was too high thus unmeasurable. Example E was unstable at FT conditions, such that its viscosity was not measured.

TABLE 2

Examples F-K

| INCI | F % | G % | H % | I % | J % | K % |
|---|---|---|---|---|---|---|
| Water | 37.60 | 6.10 | 9.50 | 52.60 | 52.60 | 49.60 |
| Cetyl Hydroxyethylcellulose | 0.30 | 0.30 | 0.15 | 0.30 | 0.30 | 0.30 |
| Glycerin | 20.00 | 55.00 | 55.00 | 5.00 | 5.00 | 5.00 |
| Magnesium Sulfate, Anhydrous | 1.00 | 1.00 | 1.00 | 1.00 | 1.00 | 1.00 |
| 1,2-Hexanediol; Caprylyl Glycol; Tropolone | 0.50 |  | 0.50 |  | 0.50 | 0.50 |
| Zinc Stearate | 0.50 | 0.50 | 0.50 | 0.50 | 0.50 | 0.50 |
| C9-15 Alkyl Phosphate |  |  |  |  |  |  |
| *Butyrospermum Parkii* (Shea) Butter | 2.00 | 2.00 | 1.00 | 2.00 | 2.00 | 2.00 |
| Polyglyceryl-2 Dipolyhydroxystearate | 3.00 | 3.00 | 3.00 | 3.00 | 3.00 | 3.00 |
| Polyglyceryl-3 Diisostearate | 2.00 | 2.00 | 2.00 | 2.00 | 2.00 | 2.00 |
| Beeswax |  |  |  |  |  |  |
| Isopropyl Palmitate | 5.00 | 5.00 | 5.00 | 5.00 | 5.00 | 5.00 |
| Dicaprylyl Carbonate | 5.00 | 2.00 | 0.00 | 5.00 |  |  |
| Sorbitan Sesquioleate |  |  |  |  | 2.00 | 5.00 |
| Microcrystalline Wax | 1.00 | 1.00 | 0.25 | 1.00 |  |  |
| Zinc Oxide | 13.00 | 13.00 | 13.00 | 13.00 | 13.00 | 13.00 |
| *Avena Sativa* (Oat) Kernel Extract; Glycerin; Water | 0.10 | 0.10 | 0.10 | 0.10 | 0.10 | 0.10 |
| Citric Acid |  |  |  |  |  |  |
| Lanolin | 4.00 | 4.00 | 4.00 | 4.00 | 4.00 | 4.00 |
| C12-15 Alkyl Benzoate | 5.00 | 5.00 | 5.00 | 5.00 | 3.50 | 3.50 |
| Patrolatum |  |  | 2.00 |  |  |  |
| Phenoxyethanol |  |  |  |  | 5.00 | 5.00 |
| Trimethylsiloxysilicate |  |  |  | 0.50 | 0.50 | 0.50 |

Example F had a viscosity of 13,000 cps and was found to be stable. Example G was unstable after 4 weeks of formation. Example H was found to be unstable in less than 1 week. Example I was unstable at 8 weeks. Example J was found to be too "runny", therefore had unsuitable viscosity. By contrast, Example K was found to have too high of a viscosity; it was found to have a viscosity of 41,000 cps after 4 weeks which was undesirable even though its initial viscosity was about 27,000 cps.

TABLE 3

Examples L-Q

| INCI | L % | M % | N % | O % | P % | Q % |
|---|---|---|---|---|---|---|
| Water | 22.60 | 56.40 | 15.90 | 55.90 | 0.00 | 52.95 |
| Cetyl Hydroxyethylcellulose | 0.30 | 0.00 | 0.00 | 0.00 | 0.00 | 0.00 |
| Glycerin | 5.00 | 3.00 | 10.00 | 3.00 | 5.00 | 5.00 |
| Magnesium Sulfate, Anhydrous | 0.00 | 1.00 | 1.00 | 1.00 | 0.00 | 1.00 |
| 1,2-Hexanediol; Caprylyl Glycol; Tropolone | 0.50 | 0.50 | 0.50 | 0.50 | 0.00 | 0.50 |
| Zinc Stearate | 0.00 | 0.50 | 0.00 | 0.50 | 0.00 | 0.50 |
| C9-15 Alkyl Phosphate | 0.00 | 0.00 | 0.00 | 0.00 | 0.00 | 3.00 |
| *Butyrospermum Parkii* (Shea) Butter | 0.00 | 2.00 | 0.00 | 2.00 | 0.00 | 2.00 |
| Polyglyceryl-2 Dipolyhydroxystearate | 3.00 | 3.00 | 3.00 | 3.00 | 0.00 | 3.00 |
| Polyglyceryl-3 Diisostearate | 2.00 | 2.00 | 2.00 | 2.00 | 0.00 | 3.00 |
| Beeswax | 0.00 | 0.00 | 0.00 | 0.00 | 0.00 | 0.00 |
| Isopropyl Palmitate |  | 5.50 | 0.00 | 5.50 | 0.00 | 5.00 |
| Dicaprylyl Carbonate | 0.00 | 5.00 | 0.00 | 5.00 | 0.00 | 2.50 |
| Dicaprylyl Ether |  |  |  |  |  |  |
| Sorbitan Sesquioleate | 8.00 | 0.00 | 8.00 | 0.00 | 5.00 |  |
| Microcrystalline Wax | 1.00 | 0.00 | 1.00 | 0.00 | 5.00 | 1.00 |
| Zinc Oxide | 13.00 | 13.00 | 13.00 | 13.00 | 13.00 | 13.00 |
| *Avena Sativa* (Oat) Kernel Extract; Glycerin; Water | 0.10 | 0.10 | 0.10 | 0.10 | 0.10 | 0.10 |
| Citric Acid | 0.00 | 0.00 | 0.00 | 0.00 | 0.00 | 0.00 |
| Lanolin | 4.00 | 4.00 | 4.00 | 4.00 | 4.00 | 3.75 |
| C12-15 Alkyl Benzoate | 0.00 | 3.50 | 5.00 | 3.50 | 5.00 | 3.20 |
| Patrolatum |  |  | 20.00 |  | 0.00 |  |
| Mineral Oil | 40.00 | 0.00 | 15.00 | 0.00 | 61.90 |  |
| Phenoxyethanol | 0.50 | 0.50 | 0.50 | 0.50 | 0.00 | 0.50 |
| Trimethylsiloxysilicate |  |  | 1.00 | 0.50 | 1.00 |  |

Examples L and Q were found to be unstable at the time of manufacturing the samples. Example M was unstable at 2 weeks at a temperature of 50° C. Example N was found to be too water thin and was not a true emulsion. Example O was found to be stable and had a viscosity of 10,000 cps. Example P did not achieve the desired foaming profile.

TABLE 4

Examples R-V

| INCI | R % | S % | T % | U % | V % |
|---|---|---|---|---|---|
| Water | 44.16 | 45.65 | 56.95 | 57.45 | 56.95 |
| Cetyl Hydroxyethylcellulose | 0.00 | 0.00 | 0.00 | 0.00 | 0.00 |
| Glycerin | 3.00 | 3.00 | 3.00 | 3.00 | 3.00 |
| Magnesium Sulfate, Anhydrous | 1.00 | 1.00 | 1.00 | 1.00 | 1.00 |
| 1,2-Hexanediol; Caprylyl Glycol; Tropolone | 0.50 | 0.50 | 0.50 | 0.50 | 0.50 |
| Zinc Stearate | 0.80 | 0.80 | 0.50 | 0.50 | 0.50 |
| C9-15 Alkyl Phosphate | 5.50 | 5.00 | 0.00 | 0.00 | 0.00 |
| *Butyrospermum Parkii* (Shea) Butter | 3.14 | 2.00 | 2.00 | 2.00 | 2.00 |
| Polyglyceryl-2 Dipolyhydroxystearate | 4.70 | 4.50 | 3.00 | 3.00 | 3.00 |
| Polyglyceryl-3 Diisostearate | 3.15 | 3.00 | 2.00 | 2.00 | 2.00 |
| Beeswax | 0.00 | 0.00 | 0.00 | 0.00 | 0.00 |
| Isopropyl Palmitate | 8.60 | 5.00 | 5.00 | 5.00 | 5.50 |
| Dicaprylyl Carbonate | 7.85 | 0.00 | 0.00 | 2.50 | 2.50 |
| Dicaprylyl Ether | | | | | |
| Sorbitan Sesquioleate | | | 0.00 | 0.00 | 0.00 |
| Microcrystalline Wax | 0.00 | 1.00 | 0.00 | 0.00 | 0.00 |
| Zinc Oxide | 13.00 | 13.00 | 13.00 | 13.00 | 13.00 |
| *Avena Sativa* (Oat) Kernel Extract; Glycerin; Water | 0.10 | 0.10 | 0.10 | 0.10 | 0.10 |
| Citric Acid | 0.00 | 0.00 | 0.00 | 0.00 | 0.00 |
| Lanolin | 4.00 | 3.75 | 3.75 | 3.75 | 3.75 |
| C12-15 Alkyl Benzoate | 0.00 | 3.20 | 3.20 | 3.20 | 3.20 |
| Patrolatum | | | | | 0.00 |
| Mineral Oil | | 8.00 | 5.00 | 2.00 | 2.50 |
| Phenoxyethanol | 0.50 | 0.50 | 0.50 | 0.50 | 0.00 |
| Trimethylsiloxysilicate | | | 0.50 | 0.50 | 0.50 |

Example R had a viscosity that was too high to be measured after 4 weeks, which was undesirable even though its initial viscosity was about 25,000 cps. Example S was found to have a viscosity of 120,000 cps after 4 weeks, which was undesirable even though its initial viscosity was about 21,000 cps. In contrast, Example T was found to be stable with a viscosity of 14,000. Example U was found to be stable with a desirable viscosity of 10,000 cps. Example V was found to be stable with a viscosity also of 10,000.

From the foregoing examples, it was found that Compositions T, U and V had suitable viscosity levels and were stable over a desired period of time for instance, at least 4 weeks or at least 8 weeks. Examples T and U included phenoxyethanol as well as Trimethylsiloxysilicate, while Example V contained Trimethylsiloxysilicate but was free of phenoxyethanol. It was found that compositions including an ester (e.g., C12-15 Alkyl Benzoate), a non-readily emulsifiable oil (e.g., mineral oil), and a flake resin (e.g., trimethylsiloxysilicate) provided improved viscosity levels, foaming, foam drainage, and stability.

What is claimed is:

1. A foamable composition for dispensing from a spray container and consisting of:
   a. water in an amount of from 40% to 60% by weight of the composition;
   b. from 3.0% to 5% of $C_{12}$-$C_{15}$ alkyl benzoate by weight of the composition;
   c. an oil, wherein the oil is selected from the group consisting of mineral oil and petrolatum;
   d. from 0.2% to 1.0% trimethylsiloxysilicate by weight of the composition;
   e. from 10% to 20% of zinc oxide by weight of the composition; and
   f. from 1% to 5% of glycerin by weight of the composition;
   g. from 1% to 5% of magnesium sulfate by weight of the composition;
   h. from 1% to 10% of polyglyceryl-2 dipolyhydroxystearate by weight of the composition;
   i. from 5% to 20% of isopropyl palmitate by weight of the composition;
   j. up to 5% of *Butyrospermum parkii* (shea) butter by weight of the composition;
   k. from 1% to 10% of polyglyceryl-3 diisostearate by weight of the composition;
   l. From 0.1% to 1.0% of *Avena sativa* kernel extract by weight of the composition;
   m. from 1% to 5% of zinc stearate by weight of the composition;
   n. from 5% to 20% of dicaprylyl carbonate by weight of the composition;
   o. up to 5% of lanolin by weight of the composition;
   p. from 0.1% to 1% of a mixture of 1,2-hexanediol; caprylyl glycol; tropolone by weight of the composition; and
   a propellant selected from the group consisting of propane, butane, isobutane, pentane, ethane, isopentane, methyl ether, difluoroethane, and combinations thereof;
   wherein the trimethylsiloxysilicate maintains bubble formation in the composition;
   wherein the foamable composition is foamed upon dispensing from the spray container, and wherein the foamed composition has a foam drainage time of 30 seconds to 2 minutes;
   wherein the viscosity of the foamable composition is from 10,000 cps to 40,000 cps at 25° C., as measured using a Brookfield RVDV-II+Pro viscometer at ambient temperature; and
   wherein the foamable composition is stable for at least four weeks.

2. A method of dispensing a composition from a dispenser comprising the steps of: (a) aligning an exit port of the dispenser at a target site, wherein the exit port is biased in a closed position and is openable upon activation, wherein the dispenser includes the foamable composition of claim 1; and (b) activating the exit port at the target site to open the exit port, thereby dispensing a desired amount of the foamable composition at the target site.

3. The method of claim 2, wherein the target site is human skin.

4. The method of claim 2, wherein the dispenser further includes an inorganic compound.

5. The method of claim 2, wherein a weight ratio of trimethylsiloxysilicate to $C_{12}$-$C_{15}$ alkyl benzoate is in the range of from 1:2 to 2:1.

6. The method of claim 2, wherein the propellant is present in the dispenser in an amount of from 6% to 8% by weight of the contents of the dispenser.

7. A system for dispensing a composition from a spray container, the system comprising: (a) the foamable composition of claim 1; and (b) a dispenser having an exit port that is biased in a closed position and is openable via an opening action.

8. The foamable composition of claim 1, wherein trimethylsiloxysilicate is present in the amount of 0.5% by weight of the composition.

9. The system of claim 7, wherein trimethylsiloxysilicate in the foamable composition is present in the amount of 0.5% by weight of the composition.

* * * * *